United States Patent [19]

Misaki et al.

[11] Patent Number: 4,556,634
[45] Date of Patent: Dec. 3, 1985

[54] HIGH SENSITIVITY ASSAY METHOD

[75] Inventors: Hideo Misaki; Masahiko Taniuchi, both of Shizuoka, Japan

[73] Assignee: Toyo Jozo Kabushiki Kaisha, Shizuoka, Japan

[21] Appl. No.: 506,844

[22] Filed: Jun. 22, 1983

[51] Int. Cl.$^4$ .......................... C12Q 1/26; C12Q 1/32
[52] U.S. Cl. ........................................ 435/25; 435/26
[58] Field of Search .................................. 435/26, 25

[56] References Cited

PUBLICATIONS

Bergmeyer-Methods of Enzymatic Analysis vol. 1, (1974) (Acad. Press) pp. 136–143 (Article by Mollering et al.).

Primary Examiner—Sam Rosen
Attorney, Agent, or Firm—Young & Thompson

[57] ABSTRACT

A high sensitivity assay method of the coenzyme cyclic assay type, eliminates the need for a separate indication reaction, by using the cycling reaction itself as the indication reaction, according to the following steps:

(1) Main reaction system:

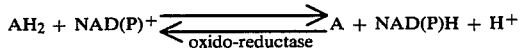

$$AH_2 + NAD(P)^+ \underset{\text{oxido-reductase}}{\rightleftarrows} A + NAD(P)H + H^+$$

wherein $AH_2$ or $A$: substance to be assayed;

$NAD(P)^+$: $NAD^+$ or $NADP^+$;

$NAD(P)H$: reduced form of $NAD^+$ or $NADP^+$;

(2) Decomposition reaction:

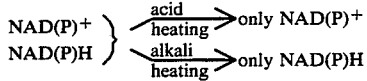

$$NAD(P)^+ \xrightarrow{\text{acid heating}} \text{only } NAD(P)^+$$
$$NAD(P)H \xrightarrow{\text{alkali heating}} \text{only } NAD(P)H$$

Neutralization:
Neutralization of alkali:

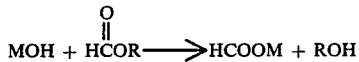

$$MOH + HCOR \rightarrow HCOOM + ROH$$

wherein M: alkali metal and R: lower alkyl;

(3) Cycling reaction:

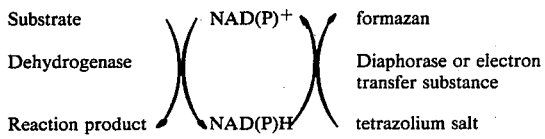

the thus-formed formazan is then colorimetrically measured, to give a highly sensitive determination of the quantity of the substance to be assayed, e.g. $NAD^+$, $NADP^+$, malic acid or γ-aminobutyric acid in human serum.

17 Claims, 5 Drawing Figures

△: GABA STANDARD AQUEOUS SOLUTION

HIGH SENSITIVITY ASSAY METHOD

This invention relates to a high sensitivity assay method.

Heretofore, fluorescent assay methods, luminescent assay methods and other methods have been used as high sensitivity assay methods. However, in these methods, errors in the assay of specimens such as body fluids arise, due to contaminants in the body fluids.

Coenzyme cyclic assay methods are also known. However, in these prior methods, an indication reaction is required after the cycling reaction, which requires a complicated technique, and the indication reaction itself is affected by substances other than the substance to be assayed. Furthermore, a special reaction vessel is required for fatty material and large reaction volumes are involved.

Moreover, in the prior methods, unreacted coenzyme to be decomposed is decomposed by adding acid or alkali, and heating and neutralizing the reaction mixture. In thse operations, it is important to add the exact amount of acid or alkali in order to neutralize the reaction mixture, for if the pH of the neutralized reaction mixture varies, the ratio of cycling is adversely affected. These phenomena thus give rise to errors in the assay.

We have found that, in the cycling reaction, the cycling reaction can itself be used as the indication reaction, thus avoiding the need for a separate indication reaction and separate indication reagents. Furthermore, end-point assay and rate assay methods thus become possible, and no special reaction vessel is required.

We have also found that pH adjustment is easily achieved by adding an excess of a formic acid lower alkyl ester, in order to avoid affecting the cycling rate due to variations of pH from neutral pH.

Accordingly, it is an object of the present invention to provide an assay method in which the cycling reaction itself is the indication reaction, without the need for separate operations and reagents for indication purposes, and without affecting any substance other than the substance to be assayed.

Another object of the present invention is to provide an assay method not only for end-point assay but also for rate assay.

A further object of the present invention is to provide a simple assay method without requiring a special reaction vessel, without requiring large reaction volumes, and which can be performed in a conventional constant temperature box.

A still further object of the present invention is to provide an assay method in which the pH of the reaction mixture can easily be adjusted by adding an excess of a formic acid lower alkyl ester in order to avoid errors in measurement caused by the cycling ratio being affected by variations in the pH in case the exact amount of acid or alkali is not added upon neutralization of the reaction after the decomposition of unreacted coenzyme.

Still another object of the present invention is to provide an assay method that does not require purification and concentration of the substance to be assayed.

The outline of the present invention is as follows:

(1) Main reaction system:

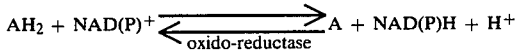

wherein $AH_2$ or $A$: substance to be assayed;

$NAD(P)^+$: $NAD^+$ or $NADP^+$;

$NAD(P)H$: reduced form of $NAD^+$ or $NADP^+$;

(2) Decomposition reaction:

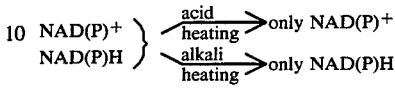

Neutralization:

Neutralization of alkali:

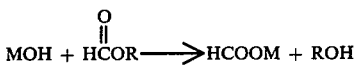

wherein M: alkali metal and R: lower alkyl;

(3) Cycling reaction:

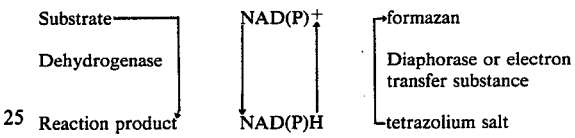

In this invention, the oxido-reductase used in the main reaction is not limited and has an action on the substance to be assayed as a substrate together with $NAD(P)^+$ or $NAD(P)H$ as a coenzyme. These enzymes can be either novel enzymes or known enzymes. Examples of known enzymes and substrates are to be found in "Enzyme Handbook", (Shiro Akabori Ed., Asakura Publishing Co., Tokyo).

The amount of the reaction mixture can vary between 3 ml and 10 ml. The amount of the coenzyme is 10 m moles to 0.1 mole. The minimum measurable amount of the substance to be assayed is $10^{-15}$-$10^{-8}$ mole, and the amount of coenzyme is in excess of stoichiometric.

The above reaction proceeds at the optimum pH of the oxido-reductase and at optimum temperatures. Next, the unreacted coenzyme is decomposed at the end-point of the main reaction. In this decomposition reaction system, in the case of oxidized coenzyme $NAD^+$ or $NADP^+$, alkali is added and the mixture is heated to produce the reduce coenzyme, NADH or NADPH, in the main reaction. Also, $NAD^+$ or $NADP^+$ is produced by adding acid and heating, in case the unreacted coenzyme is NADH or NADPH. Examples of alkali are usually alkali hydroxides such as aqueous sodium hydroxide or potassium hydroxide. Aqueous lithium hydroxide, sodium carbonate or potassium carbonate can also be used.

The concentration of the alkali should be such that the pH of the solution is alkaline and more particularly over pH 12. The preferred concentration range of the alkali is 0.0001 M–0.5 M.

The heating conditions will vary depending on the alkali concentration, the temperature and the heating time. $NAD^+$ or $NADP^+$ is completely decomposed at 100° C. in 10 mins. in a 0.1N NaOH solution.

The concentration of the acid is such that the pH of the aqueous solution is below pH 2. Examples of suitable acids are hydrochloric acid or sulfuric acid. The preferred concentration range of the acid is 0.001 M–0.5 M. The heating conditions will vary depending on the acid concentration, the temperature and the heating time. For example, NADH or NADPH can be decomposed at 50° C. in 3 mins. in 0.1N HCl.

In the neutralization reaction stage after decomposition of unreacted coenzyme, in the case in which NAD+ or NADP+ is decomposed by alkali, the reaction mixture is neutralized by adding a formic acid lower alkyl ester. Examples of formic acid lower alkyl esters are methyl formate, ethyl formate, propyl formate or butyl formate. In the conventional method, the desired pH of the reaction mixture is missed if the addition of acid is not exactly performed, and the ratio of cycling varies thereby causing an error in the assay value. However, in the neutralization reaction of the present invention, even if an excess amount of a formic acid lower alkyl ester is used in the neutralization, for example 10 times the amount necessary for neutralization, is added, nevertheless only the stoichiometric amount of formic acid lower alkyl ester will react, and hence exact neutralization of the reaction mixture can be achieved and pH adjustment can thus easily be performed.

In the case in which NADH or NADPH is decomposed by acid, a slight excess of alkali is added for neutralization, followed by adding a formic acid lower alkyl ester the same as hereinabove for neutralization, whereby the reaction mixture can be exactly neutralized.

An example of the alkali is an aqueous solution of alkali hydroxide, as above.

The next step of the reaction of the present invention, namely, the amplifying reaction by coenzyme cycling, can be carried out by combining the oxido-reductase system, which acts on the remaining coenzyme to convert it to the corresponding substance to be assayed and an excess amount of substrate, and the converting system in which tetrazolium salt is converted to formazan by diaphorase or an electron transfer substance. The oxido-reductase of the system hereinabove is not limited in its origin, and is a dehydrogenase which requires coenzyme NAD(P)+ and forms NAD(P)H by acting on an excess amount of a specific substance.

Embodiments of these enzymes and substrates are found in "Enzyme Handbook" hereinbefore mentioned.

The amount of enzyme used depends on the enzyme activity, the kind of substrate and the ratio of coenzyme cycling.

The molar amount of substrate should be a larger excess than that of the cycling coenzyme and can be at a concentration more than that for the maximum reaction rate of the said oxidoreductase, reductase, and is preferably present in a concentration of 0.1–50 U/ml in the reaction mixture. Examples of the electron transfer substances are substances having oxidizing activity on NAD(P)H to NAD(P)+ and without any detrimental action on the coenzyme cycling reaction, for example, phenazine methosulfate, Meldola's Blue and pyrocyanine. The concentration thereof can be selected according to the ratio of cycling and is preferably 1 $\mu$g/ml–1 mg/ml of the reaction mixture. Examples of tetrazolium salts are 3,3'-(3,3'-dimethoxy-4,4'-diphenylene) bis [2-(p-nitrophenyl)-5-phenyl-tetrazoliumchloride](NTB), 2-(p-nitrophenyl)-3-(p-iodophenyl)-5-phenyltetrazoliumchloride (INT) or 2-(4,5-dimethyl-2'-thiazolyl)-3,5-diphenyltetrazoliumbromide(4,5-MTT). The concentration of the tetrazolium salt is rather limited by the solubilities of tetrazolium salts and the ultimately formed formazan and is 3–100 mg/ml of the reagent.

The cycling reaction can be carried out at room temperature to 37° C., preferably at 30°–37° C. The reaction can be terminated at estimated time of its end point by adding an acid such as hydrochloric acid or phosphoric acid. A surface active agent can preferably be added in order to avoid the precipitation of formazan.

Examples of surface active agents are non-ionic surface active agents such as Triton X-100 or Adekarol SO-14 (trade names). The concentration of the surface active agent is 0.01–3% by weight of the reagent. The addition of the surface active agent provides an increase in sensitivity of the assay and a stabilization of the formazan pigment. Colorimetric assay of the thus-formed formazan pigment can be performed by measuring the optical density (OD) at the specific absorption wavelength of formazan, for example 500–550 nm.

Various substances can be assayed by the method hereinabove explained. According to the method of the present invention, not only the end-point assay but also the rate assay can be performed.

The following examples illustrate the present invention but are not to be construed as limiting:

EXAMPLE 1

Quantitative assay of NAD+:

[Reagent]
(1) 0.2 M phosphate buffer solution (pH 8.0)
(2) INT-Adekatol solution [INT (100 mg) dissolved in 2% Adekatol-SO-145 solution (100 ml)]
(3) Diaphorase or electron transfer substance
   (a) diaphorase (NADH) solution 100 U/ml.
   (b) phenazine methosulfate (PMS) solution 100 mg/20 ml.
   (c) pyrocyanine solution 10 mg/20 ml.
   (d) Meldola's Blue solution 10 mg/20 ml.
(4) Ethanol
(5) Alcohol dehydrogenase 250 U/ml.
(6) 10 mM NAD+ solution (In the main reaction, NAD+ is formed and unreacted NADH is decomposed by acid and heating, then neutralized with alkali, and further completely neutralized with ethyl formate.)
(7) 0.1 N HCl

[Operation]

Figure 1:
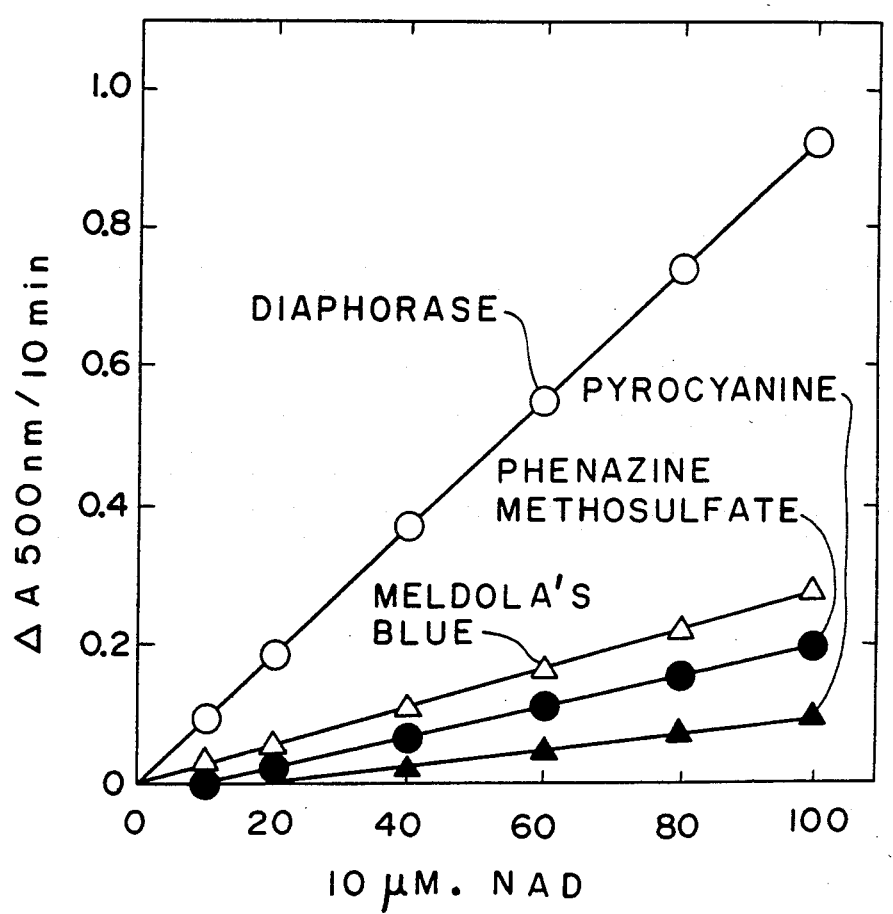
FIG. 1 is the standard curves of NAD+ using diaphorase and other electron transfer substances as an indication reaction.

In each of seven separate test tubes, phosphate buffer (0.5 ml), INT-Adekatol (0.2 ml), ethanol (20 $\mu$l), water (30 $\mu$l) and alcohol dehydrogenase (0.1 ml) were admixed. Diaphorase (NADH) or electron transfer substance (50 $\mu$l) was added thereto, and each mixture was incubated at 37° C. for 3 mins. Thereafter 10 $\mu$M NAD+ solution (0, 10, 20, 40, 60, 80 or 100 $\mu$l) was added thereto, respectively, and each volume thereof was adjusted to a total of 1.0 ml and each mixture was incubated at 37° C. for exactly 10 mins. 0.1 N HCl (2 ml) was added to each tube to stop the reaction, and the OD was measured at 50 nm. Water (0.1 ml) was added in place of NAD as a control.
[Results]
The results are shown in FIG. 1, in which the amount of NAD together with diaphorase or electron transfer substance and absorption optical density have good linearity. The results show that there was an exact cycling reaction of high sensitivity.

EXAMPLE 2

The effect of the oxido-reductase used in the cycling reaction is shown as follows:
[Reagent]
(1) 0.12 M phosphate buffer pH 8.0
(2) INT-Adekatol solution (same as in Example 1)
(3) diaphorase (NADH) solution
(4) substrate solution
  (a) 100 mM ethyl alcohol
  (b) 100 mM glycerol-3-phosphate solution
  (c) 100 mM lactic acid
  (d) 100 mM malic acid
(5) oxido-reductase
  (a) alcohol dehydrogenase (ADH) solution 25000 U/ml
  (b) glycerol-3-phosphate dehydrogenase (G-3-PDH) solution 600 U/ml
  (c) lactate dehydrogenase (LDH) solution 1500 U/ml
  (d) malate dehydrogenase (MDH) solution 4600 U/ml
  (e) 10 $\mu$M NAD+ solution
  (f) 0.1 N HCl
[Operation]
In each of seven separate test tubes, phosphate buffer (0.5 ml), INT-Adekatol (0.2 ml), diaphorase (NADH) (50 $\mu$l), substrate solution (50 $\mu$l), oxido-reductase acting on the above substrate (5 $\mu$l) and water (95 $\mu$l) were admixed, and each mixture was incubated at 37° C. for 3 mins.

Figure 2:
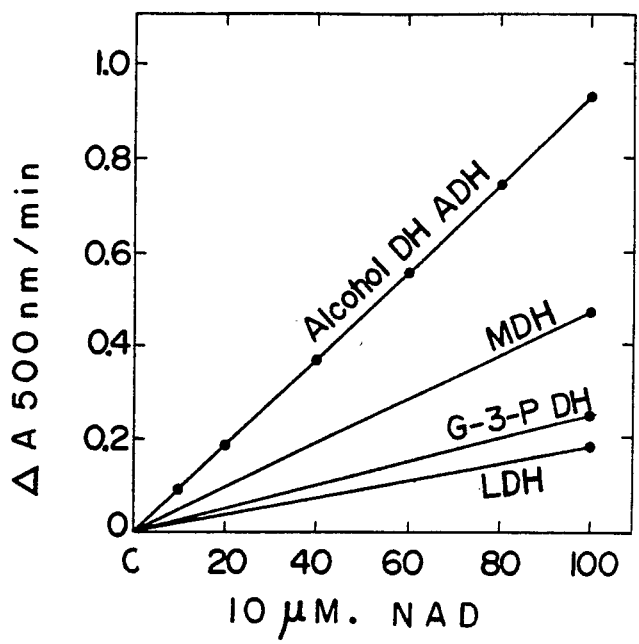
FIG. 2 is the standard curves of NAD+ showing the effect of the oxido-reductase used in the cycling reaction.

10 $\mu$M NAD+solution (0, 10, 20, 40, 60, 80 or 100 $\mu$l) was added thereto, respectively, and each mixture was adjusted to a total volume of 10 ml and incubated at 37° C. for exactly 10 mins. 0.1 N HCl (2 ml) was added to each tube to stop the reaction, and the OD was measured at 500 nm. Water (100 $\mu$l) was used in place of NAD+ solution as a control.
[Results]
The results are shown in FIG. 2. For each oxido-reductase, good linearity is shown and indicates the exactness of the cycling reaction and its high sensitivity.

EXAMPLE 3

Figure 3:
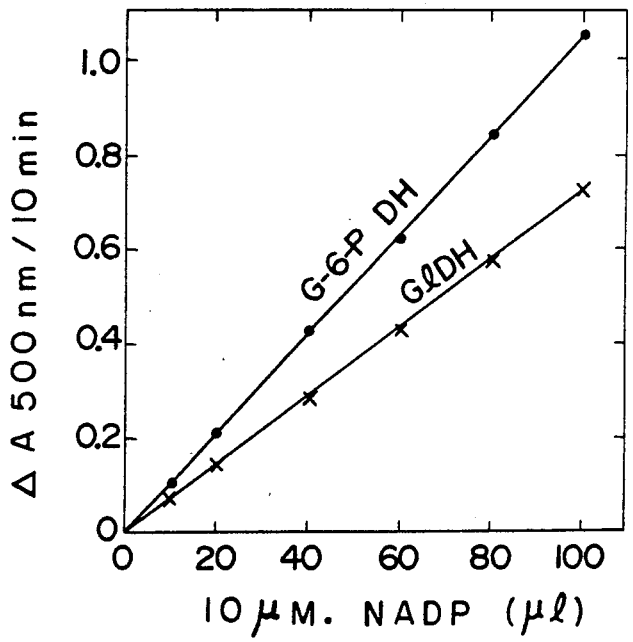
FIG. 3 is the standard curve of NADP+ showing the effect of the oxido-reductase used in the cycling reaction.

Quantitative assay of NADP+:
[Reagent]
(1) 0.2 M phosphate buffer pH 8.0
(2) INT-Adekatol solution [INT (100 mg) dissolved in 2% Adekatol SO-145 solution (100 ml)]
(3) NADPH-diaphorase (NADPH) solution 100 U/ml
(4) Substrate soltuion
  (a) 100 mM glucose-6-phosphate (G-6-P)
  (b) 100 mM glutamic acid (GA)
(5) Oxido-reductase solution
  (a) glucose-6-phosphate dehydrogenase (G-6-PDH) solution 1000 U/ml
  (b) glutamate dehydrogenase (GlDH) solution 1000 U/ml
(6) 10 $\mu$M NADP+ solution
(7) 0.1 N HCl
[Operation2]
In each of seven separate test tubes, phosphate buffer (0.5 ml), INT-Adekatol (0.1 ml), diaphorase (NADPH) (100 $\mu$l), substrate (50 $\mu$l), enzyme (50 $\mu$l) and water (30 $\mu$l) were admixed, and each mixture was incubated at 37° C. for 3 mins., then 10 $\mu$M NADP+ (0, 10, 20, 40, 60, 80 and 100) was added respectively therein. The total volume of each mixture was adjusted to 1.0 ml by adding water, and then each mixture was incubated at 37° C. exactly for 10 mins. 0.1 N HCl (2 ml) was added to each tube to stop the reaction, and the OD was measured at 500 nm. Water (100 $\mu$l) was added in place of NADP solution as a control.
[Results]
The results are shown in FIG. 3, in which good linearity was obtained, and so it is shown that NADP+ can be assayed with high sensitivity together with glucose-6-phosphate dehydrogenase and glutamate dehydrogenase.

EXAMPLE 4

Figure 4:
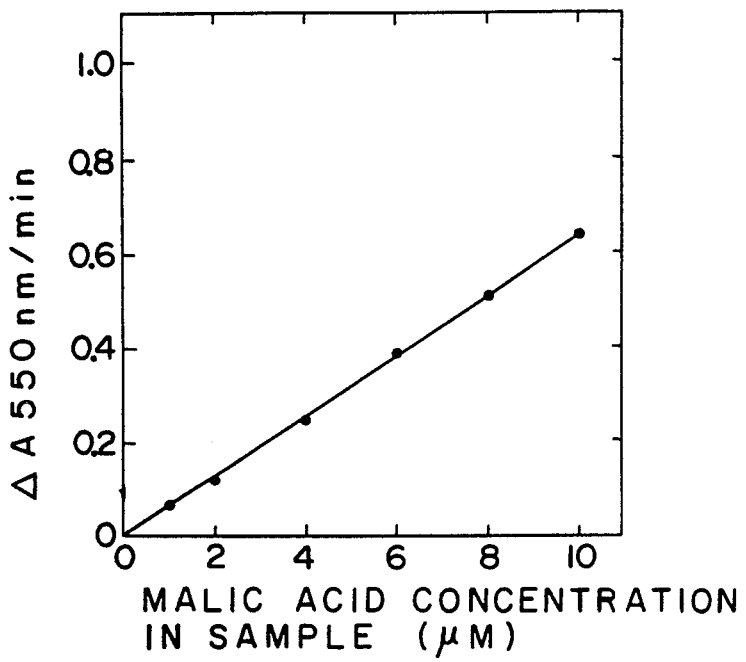
FIG. 4 is the malic acid standard curve.

Quantitative assay of malic acid:
[Sample]
Malic acid solution (malic acid; 0, 1, 2, 4, 6, 8 and 10 $\mu$M) 20 $\mu$l.
[Reagent]
(1) Reagent I: mixed solution of 0.2 M phosphate buffer pH 8.0 (0.2 ml), 10 mM NAD+ solution (0.1 ml) and malate dehydrogenase (120 U/ml) solution (100 $\mu$l).
(2) 0.2 N NaOH
(3) ethyl formate
(4) Reagent II: mixed solution of 0.5 M phosphate buffer pH 8.0 (0.1 ml), ethyl alcohol (10 $\mu$l), alcohol dehydrogenase (250 U/ml) (50 $\mu$l), diaphorase (NADH) (100 U/ml) (100 $\mu$l), 1% NTB solution (20 $\mu$l) and Triton X-100 solution (20 $\mu$l).
(5) 0.1 N HCl
[Operation]
The above seven maclic acid solutions were introduced into respective ones of separate test tubes, and the reagent I (0.2 ml) was added to each. Each mixture was then incubuated at 37° C. for 15 mins. 0.2 N NaOH (0.1 ml) was added to each reaction mixture, and was heated at 100° C. for 10 mins., then immediately cooled, and then neutralized with ethyl formate (20 $\mu$l). After incubation at 37° C. for 5 mins., reagent II (0.3 ml) was added to each, and each was incubated at 37° C. for exactly 10 mins. 0.1 N HCl (2.5 ml) was added to stop the reaction, and the OD at 550 nm was measured. Water (100 $\mu$l) was used in place of NAD+ solution as a control.
[Results]
The results are shown in FIG. 4. The amount of malic acid is related to OD with less error. Malic acid was thus shown to be assayed with high sensitivity.

EXAMPLE 5

Quantitative assay of $\gamma$-aminobutyric acid:
[Sample]
Seven aliquots of human serum (50 $\mu$l), in which $\gamma$-aminobutyric acid (GABA) (0, 10, 20, 30, 40 and 50 $\mu$M) was respectively admixed.
[Reagent]
(1) Reagent I: mixed solution of 0.1 M pyrophosphate buffer, pH 8.3 (1.0 ml), 10 mM NADP+ solution (0.2 ml), 0.1 M $\alpha$-ketoglutarate soltuion (1.0 ml)

and GABASE (2 U/ml, 0.4 ml, commercially available enzyme from *Pseudomonas fluorescens*).

(2) 0.5 N NaOH solution (3) ethyl formate (4) Reagent II: mixed solution of INT-Adekatol solution [0.1 ml, INT (100 mg) dissolved in 2% Adekatol SO-145 solution (100 ml)], diaphorase (NADPH) solution (100 U/ml, 1.0 ml), 0.1 M glucose-6-phosphate solution (0.2 ml) and glucose-6-phosphate dehydrogenase solution (100 U/ml, 2.0 μl).

[Operation]

Reagent I (0.35 ml) was added to each sample and each was incubated at 37° C. for 30 mins. 0.5 N NaOH (0.1 ml) was added to each sample and each was heated at 100° C. for 10 mins. After cooling, ethyl formate (20 μl) was added to each sample for neutralization, and each was incubated at 37° C. for 5 mins. Reagent II (0.2 ml) was added to each and each was incubated at 37° C. for exactly 10 mins. 0.1N HCl (2 ml) was added to each to stop the reaction and the OD at 500 nm was measured. A control without GABA was used.

[Results]

Figure 5:
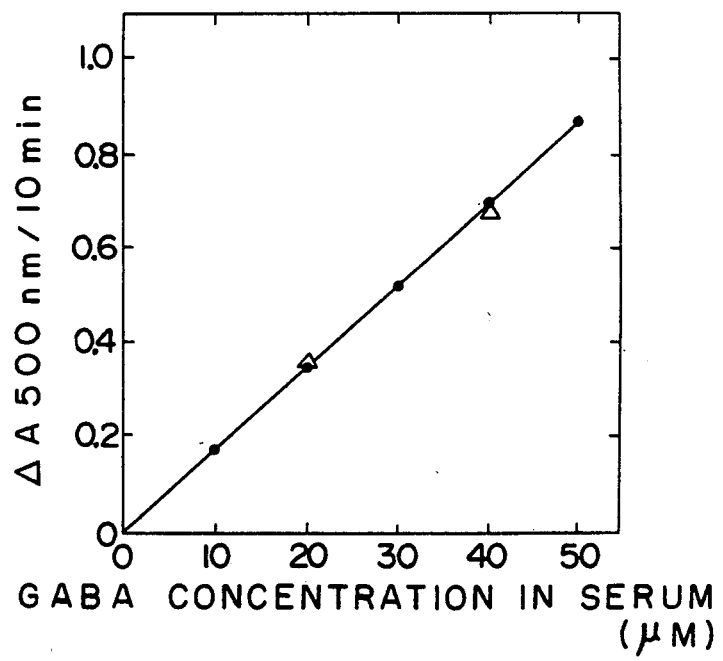
FIG. 5 is the standard curve of GABA added to human serum.

The results are shown in FIG. 5. The amount of GABA in human serum can be spotted on the linear line in relation to the OD value. GABA can thus be assayed with high sensitivity and without separating the protein.

What is claimed is:

1. In a high sensitivity assay method for a substance to be assayed, comprising
   (1) converting the coenzyme corresponding to an amount of substance to be assayed, by the action of an oxide-reductase for the said substance, in the presence of coenzyme NAD+ or NADH, or NADP+ or NADPH;
   (2) performing a cycling reaction by coenzyme cycling consisting of a combination of an oxido-reduction reaction which acts on excess substrate and coenzyme converted corresponding to the amount of the substnce to be assayed, and a conversion reaction from tetrazolium salt to formazan in the presence of diaphorase or electron transfer substance; and
   (3) colorimetrically measuring the thus-formed formazan; the improvement comprising decomposing and neutralizing unreacted coenzyme at the end of said converting by adding a formic acid lower alkyl ester.

2. An assay method according to claim 1, wherein the molar ratio of coenzyme in the main reaction system is in stoichiometric excess as compared with the molar ratio of the substance to be assayed.

3. An assay method according to claim 1, wherein unreacted coenzyme in case of NAD+ and NADP+ is decomposed by adding an aqueous alkali hydroxide and heating prior to neutralizing.

4. An assay method according to claim 3, wherein the concentration of the aqueous alkali hydroxide is such as to raise the pH above 12.

5. An assay method according to claim 4, wherein the alkali hydroxide is sodium hydroxide or potassium hydroxide.

6. An assay method according to claim 3, wherein the heating is carried out until complete decomposition of NAD+ or NADP+.

7. An assay method according to claim 1, wherein unreacted coenzyme, in case of NADH or NADPH, is decomposed by adding aqueous acid and heating prior to neutralizing.

8. An assay method according to claim 7, wherein the concentration of aqueous acid is such as to lower the pH to below 2.

9. An assay method according to claim 8, wherein the acid is hydrochloric acid or sulfuric acid.

10. An assay method according to claim 7, wherein the heating is carried out until complete decomposition of NADH or NADPH.

11. An assay method according to claim 7, wherein the neutralization is carried out by adding a small excess of alkali hydroxide solution and immediately adding formic acid lower alkyl ester.

12. An assay method according to claim 11, wherein said alkali hydroxide is sodium hydroxide or potassium hydroxide.

13. An assay method according to claim 8, wherein said formic acid lower alkyl ester is methyl formate, ethyl formate, propyl formate or butyl formate.

14. An assay method according to claim 11, wherein said formic acid lower alkyl ester is methyl formate, ethyl formate, propyl formate or butyl formate.

15. An assay method according to claim 1, wherein the electron transfer substance in the cycling reaction is phenazine methosulfate, Meldola's blue or pyrocyanine.

16. An assay method according to claim 1, wherein a surface active agent is added.

17. An assay method according to claim 16, wherein the surface active agent is a non-ionic surface active agent.

* * * * *